United States Patent

Jean et al.

[11] Patent Number: 6,036,683
[45] Date of Patent: *Mar. 14, 2000

[54] PROCESS AND APPARATUS FOR CHANGING THE CURVATURE OF THE CORNEA

[75] Inventors: Benedikt Jean; Thomas Bende; Theo Ottrup; Michael Mataliana; Rudolf Walker, all of Tuebingen, Germany

[73] Assignee: G. Rodenstock Instruments GmbH, Ottobrunn-Riemerling, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/778,186

[22] Filed: Jan. 2, 1997

[51] Int. Cl.[7] .................................................. A61B 17/36

[52] U.S. Cl. .................................................. 606/5; 606/16

[58] Field of Search .................................. 606/5, 16, 17

[56] References Cited

U.S. PATENT DOCUMENTS

| | | | |
|---|---|---|---|
| 5,071,417 | 12/1991 | Sinofsky | 606/8 |
| 5,112,328 | 5/1992 | Taboada et al. | 606/4 |
| 5,304,169 | 4/1994 | Sand | 606/5 |
| 5,484,432 | 1/1996 | Sand | 606/5 |
| 5,520,679 | 5/1996 | Lin | 606/5 |
| 5,549,632 | 8/1996 | Lai | 606/5 |

*Primary Examiner*—Linda C. M. Dvorak
*Assistant Examiner*—Roy Gibson
*Attorney, Agent, or Firm*—Evenson, McKeown, Edwards & Lenahan, P.L.L.C.

[57] ABSTRACT

A process is described for changing the curvature of the cornea in which the light of a light source is focused in the cornea with a wavelength of approximately 1.5 μm to 6 μm so that the collagenic tissue shrinks selectively. The invention is characterized in that the light is applied continuously at such a power that, although a temperature is reached which leads to irreversible coagulations of the collagenic tissue, the temperature within the coagulated region rises to values at which there is not yet a relaxation of the tissue.

10 Claims, 2 Drawing Sheets

PROCESS AND APPARATUS FOR CHANGING THE CURVATURE OF THE CORNEA

BACKGROUND AND SUMMARY OF THE INVENTION

The invention relates to a process and to an apparatus for changing the curvature of the cornea.

Processes and apparatus of this type are used, for example, for correcting hyperopia.

A process of the above-mentioned type and an apparatus for changing the curvature of the cornea are known, for example, from the article "Laser Thermokeratoplasty by Means of a Pulsed Holmium: YAG Laser for Hyperopic Correction" by Theo Seiler, published in *Refractive and Corneal Surgery*, Vol. 6, September/October 1990, Page 335, and on, or from U.S. Pat. No. 5,334,190 of the same content.

Additional processes and apparatus for the treatment of eyes are known from Patent Documents WO 89/06519, WO 90/12618, WO 91/00063, GB 2 228 344, EP 0 480 995 B1, EP 0 581 339 A2 or DE 40 04 423 A1.

Reference is explicitly made to the above-mentioned documents for explaining all details not explained in this documents.

All embodiments of processes and apparatus of this type known from these documents have in common that a pulsed laser is used which emits light in the infrared wavelength range.

Because of the use of a pulsed laser, the tissue on which the Laser beam is focussed is not uniformly heated. On the contrary, during the lumination, the tissue is heated by the energy entered by a laser pulse and will cool again because of thermal diffusion during the interval to the next laser pulse.

Therefore, because of the use of a pulsed laser, it is not possible to adjust the temperature in the tissue to be treated to a value which is as constant as possible and which—as described in U.S. Pat. No. 5,334,190 should be between 60° C. and 70° C.

On the contrary, in the case of the known processes and apparatuses,—as recognized according to the invention—temperature peaks may occur which are above 100° C. At these temperatures, the tissue will rapidly relax so that the endeavored treatment success of correcting a defective vision by the selective shrinking of the collagenic tissue is not achieved or is achieved only insufficiently.

It is an object of the invention to provide a process and an apparatus for changing the curvature of the cornea by means of which the defective vision of an eye and particularly hyperopia can be reliably corrected by shrinking the collagenic tissue.

According to the invention, for the selective shrinking of the collagenic tissue, the light is applied continuously at such a power that, although a temperature is reached which results in irreversible coagulations of the collagenic tissue, the temperature within the coagulated region will rise only to values at which a relaxation of the tissue does not yet occur. In this case, the light source is preferably a laser diode with a power of between 150 mW and 500 mW, preferably approximately 180 to 200 mW. In the case of such a laser diode, the lumination time for each laser spot is between 3 and 10 seconds.

Furthermore, it is preferred for the temperature in the coagulated region to be approximately 50° C. to 65° C., since, at these temperatures, a coagulation will already occur but no relaxation of the tissue. In individual cases, higher temperatures may also be used. However, it was recognized according to the invention that a relaxation may already occur starting at approximately 70° C.

By means of the approach according to the invention in which the energy required for the coagulation is applied continuously at a comparatively low power and not pulsed at a high power, a gentle treatment of the cornea is obtained in each case.

The entering of energy at a comparatively low power selected according to the invention also permits the selection of the luminous power of the light source such that, in the region of the focus cone, an approximately spherical coagulation region is formed by means of which the corneal endothelium is not impaired. This form of the coagulated region leads to a better long-term stability compared to the known processes with a pulsed entering of energy.

Furthermore, because of the gentle form of the entering of energy selected according to the invention, it is possible to place the tip of the focus cone in deeper layers of the stroma than in the case of the known methods. As a result, a particularly effective shrinking of the collagen tissue is obtained. Naturally, it is required that the depth of the focus is still sufficiently above the endothelium so the latter is not damaged or is damaged only minimally. Typical values for the depth of the focus, that is, the distance of the tip of the focus cone from the surface of the cornea, are approximately 460 μm to maximally approximately 800 μm.

In the case of an apparatus for implementing the process according to the invention, a continuously operating laser diode is preferably used as a light source whose wavelength amounts to 1.9 μm. The output power of the laser diode typically amounts to between 150 mW and 500 Mw, preferably between 180 and 200 mW. A focussing lens system focusses the light of the laser diode into the cornea. An optical fiber is preferably arranged between the laser diode and the lens system.

In the case of a laser diode, it is possible to vary the wavelength by changing the diode temperature, for example, bar means of a Peltier element. As a result, it is possible to change the depth of the focus by a variation of the wavelength of the laser diode. In this case, the diameter of the laser spot on the surface of the cornea remains virtually the same.

As an alternative or in addition, for changing the depth of the focus, the distance can be changed between the light exit surface of the optical fiber and the lens system. In this case, the diameter of the laser spot on the surface of the cornea will also change. Typically, the diameter of the laser spot is between 0.3 mm and 0.6 mm.

In a preferred embodiment of the invention, the lens system is arranged in a handpiece. In order to always ensure defined conditions, it is advantageous that the front of the lens system can be placed on the cornea because no arbitrary distance variations can occur then.

A planoconvex lens whose front is the convex surface can be used as the lens system. The lens system can be made of suitable materials which are transmitting for the wavelength of the used laser diode, such as sapphire.

Without limiting the general idea of the invention, the invention will be described in the following by means of embodiments with respect to the drawing. Explicit reference is made to the drawing with respect to the disclosure of all details of the invention which are not explained in the text.

DETAILED DESCRIPTION OF THE DRAWINGS AND SPECIFIED EMBODIMENTS

Figure 1:
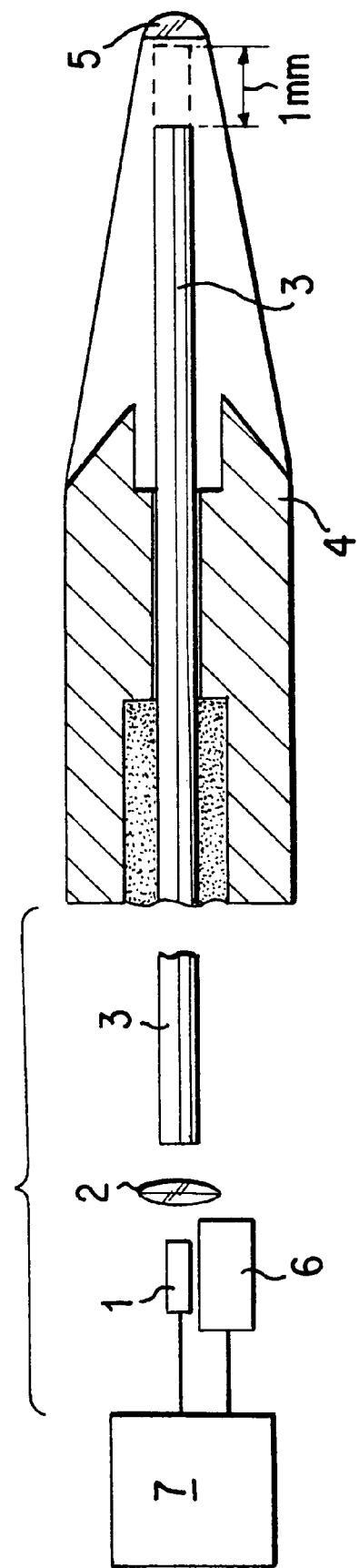
FIG. 1 is a view of an embodiment of an apparatus according to the invention.

FIG. 1 is a schematic view of the apparatus according to the invention. The apparatus has a laser diode 1 whose light is coupled into the (proximal) end of an optical fiber 3 by means of a telescope 2 which is shown only schematically and has a focal distance of, for example, 20 mm. The distal end of the optical fiber 3 is arranged in handpiece 4. At the tip of the handpiece 4, a lens 5 is situated which, in the illustrated embodiment, is a planoconvex lens and consists of sapphire. The lens 5 focusses the light emerging from the distal light exit surface of the optical fiber 3 into the cornea of an eye which is not illustrated.

For the variation of the depth of focus, the distance between the light exiting surface of the optical fiber 3 and of the lens 5 is changed.

Figure 2:
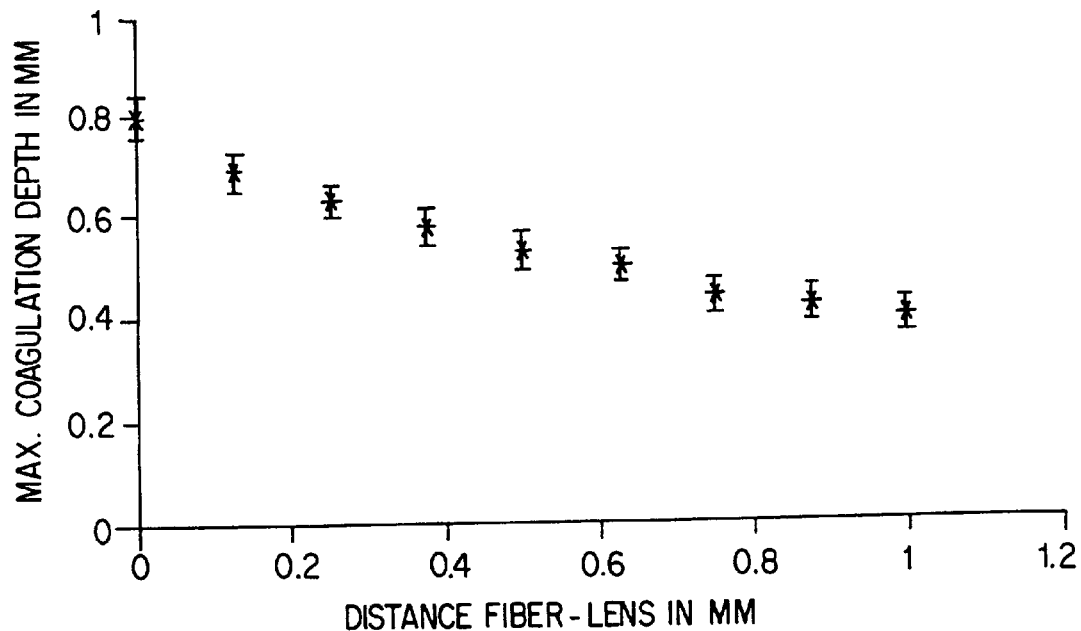
FIG. 2 is a view of the depth of focus as a function of the distance between the optical fiber and the lens system.

FIG. 2 shows the dependence of the depth of focus (in mm) on the distance between the optical fiber 3 and the lens 5 (also in mm).

With the distance, the diameter of the laser beam spot on the surface of the cornea will also change.

Figure 3:
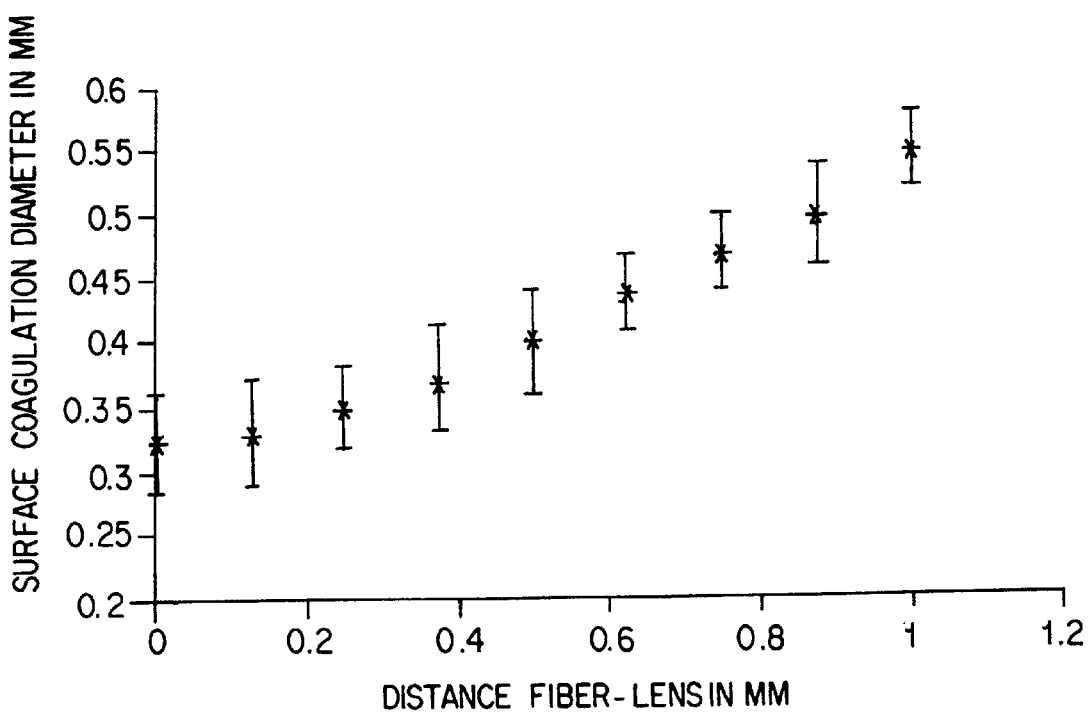
FIG. 3 is a view of the diameter of the laser spot on the surface of the cornea as a function of the distance.

FIG. 3 shows the dependence of the diameter (in mm) from the distance (in mm).

As an alternative or in addition, the depth of focus can also be changed in that the wavelength of the laser diode is varied by changing the temperature.

For this purpose, a Peltier element 6 is provided in contact with the laser diode, which element is controlled by a control unit 7 which also controls the admission of power to the laser diode 1.

When a laser diode with an emission wavelength of 1.9 $\mu$m is used at 20° C., the wavelength will fall to 1.88 $\mu$m at a temperature of 16° C. and will rise to 1.91 $\mu$m at a temperature of 21° C. Because of this wavelength shift, the depth of focus can also be varied.

In the case of a typical treatment of an eye for eliminating a hyperopia between +5 and +7, a series of coagulation spots are "set" by means of the handpiece.

The control unit 7 controls the laser diode 1 such that, at each coagulation spot, the laser diode 1 emits light of a power of approximately 180 mW for a duration of 4 to 8 seconds. In this case, the temperature in the coagulated region will rise to maximally 65° C.

The apparatus according to the invention has the advantage that the depth of focus which is critical for the successful coagulation can easily be adjusted corresponding to the appropriate application and the operating conditions.

What is claimed is:

1. A process for changing the curvature of the cornea comprising focussing light from a light source on a region of the cornea, the light having a wavelength of approximately 1.5 $\mu$m to 6 $\mu$m, so that collagenic tissue shrinks selectively, and continuously applying the light at such a power that, although a temperature is reached which leads to the irreversible coagulation of the collagenic tissue, the temperature within the coagulated region rises only to values at which a relaxation of the tissue does not occur, wherein the distance from the, tip of the focussed light to the surface of the cornea amounts to at least 460 $\mu$m and no more than 800 $\mu$m, so that the tip of the focussed light is situated in deep layers of stroma but sufficiently above the endothelium so that the endothelium is not damaged or is only minimally damaged.

2. A process according to claim 1, wherein the power of the light source is selected such that, within the region of the focussed light, an approximately spherical coagulation region is formed which does not impair the cornea endothelium.

3. A process for changing the curvature of the cornea comprising focussing light from a light source on a region of the cornea, the light having a wavelength of approximately 1.5 $\mu$m to 6 $\mu$m so that collagenic tissue shrinks selectively and continuously applying the light at such a power that, although a temperature is reached which leads to the irreversible coagulation of the collagenic tissue, the temperature within the coagulated region rises only to values at which a relaxation of the tissue does not occur, wherein the light source is a continuously operating laser diode.

4. A process according to claim 3, wherein the power of the laser diode is between 150 mW and 500 mW.

5. A process according to claim 4, wherein the laser light is focussed in an area of the cornea for between 3 and 10 seconds.

6. A process according to claim 3, comprising varying the diameter of a laser spot on the surface of the cornea by changing the distance between a light exit surface of an optical fiber and a lens system, while arranging the optical fiber between the laser diode and the lens system, whereby the optical fiber has a light entrance surface and a light exit surface.

7. A process as claimed in claim 6, comprising varying the diameter of the laser spot between 0.3 mm and 0.6 mm.

8. A process according to claim 4, comprising varying the diameter of a laser spot on the surface of the cornea by changing the distance between a light exit surface of an optical fiber and a lens system, while arranging the optical fiber between the laser diode and the lens system, whereby the optical fiber has a light entrance surface and a light exit surface.

9. A process according to claim 5, comprising varying the diameter of a laser spot on the surface of the cornea by changing the distance between a light exit surface of an optical fiber and a lens system, while arranging the optical fiber between the laser diode and the lens system, whereby the optical fiber has a light entrance surface and a light exit surface.

10. A process according to claim 1, wherein the wavelength of the laser diode is variable to change the distance from the tip of the focussed light to the surface of the cornea.

* * * * *